(12) United States Patent
Pettit et al.

(10) Patent No.: US 7,105,695 B2
(45) Date of Patent: Sep. 12, 2006

(54) SYNTHESIS OF COMBRETASTATIN A-2 PRODRUGS

(75) Inventors: George R. Pettit, Paradise Valley, AZ (US); Bryan R. Moser, Tempe, AZ (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 239 days.

(21) Appl. No.: 10/499,848

(22) PCT Filed: Dec. 20, 2002

(86) PCT No.: PCT/US02/40885

§ 371 (c)(1),
(2), (4) Date: Jun. 21, 2004

(87) PCT Pub. No.: WO03/059855

PCT Pub. Date: Jul. 24, 2003

(65) Prior Publication Data

US 2005/0075516 A1 Apr. 7, 2005

Related U.S. Application Data

(60) Provisional application No. 60/344,960, filed on Dec. 21, 2001.

(51) Int. Cl.
*C07F 9/02* (2006.01)
(52) U.S. Cl. ...................................................... 558/114
(58) Field of Classification Search ................. 558/114
See application file for complete search history.

(56) References Cited

FOREIGN PATENT DOCUMENTS

| WO | WO 99/35150 | 7/1999 |
|---|---|---|
| WO | WO 02/006279 A3 | 1/2002 |

*Primary Examiner*—Taofiq Solola

(57) ABSTRACT

The original synthesis of combretastatin A-2 (1a) was modified to provide an efficient scale-up procedure for obtaining this antineoplastic stilbene. Subsequent conversion to a useful prodrug was accomplished by phosphorylation employing in situ formation of dibenzylchlorophosphite followed by cleavage of the benzyl ester protective groups with bromotrimethylsilane to afford phosphoric acid intermediate 11. The latter was immediately treated with sodium methoxide to complete a practical route to the disodium phosphate prodrug (2a). The phosphoric acid precursor (11) of phosphate 2a was employed in a parallel series of reactions to produce a selection of metal and ammonium cation prodrug candidates. Each of the phosphate salts (2a–q) was evaluated with respect to relative solubility behavior, cancer cell growth inhibition, and antimicrobial activity.

3 Claims, No Drawings

SYNTHESIS OF COMBRETASTATIN A-2 PRODRUGS

RELATED APPLICATION

This application is the U.S. national stage of PCT/US02/40885 filed on Dec. 20, 2002, which claims the priority of U.S. Provisional Application No. 60/344,960 filed on Dec. 21, 2001, which is incorporated herein by reference.

GOVERNMENT INTEREST

The research that provides the basis for this patent was funded in part by NIH OIG CA44344-01-11. The United States government may have certain interests in this invention.

INTRODUCTION

This invention generally relates to improved methods of producing antineoplastic compounds and both water-soluble derivatives thereof which retain the same or improved bioactivity as the parent compound, and methods of synthesis thereof. More particularly this invention relates to improved methods of synthesizing combretastatin A-2, and a method of synthesizing prodrugs of combretastatin A-2.

BACKGROUND OF THE INVENTION

Without neovascularization and angiogenesis, a tumor will remain dormant and be unable to grow in size beyond a few millimeters. An exceptionally promising approach to improving human cancer treatment involves the discovery and application of new cancer antiangiogenesis drugs. Such approaches to cancer treatment may cause avascular tumors to remain dormant or eventually to undergo necrosis and shrinkage. Further, appropriate combination of antiangiogenesis with cytotoxic drugs should lead to complete elimination of the neoplastic disease.

Applicant has obtained numerous United States patents relating to the compounds of the combretastatin family. These patents are incorporated herein by reference, and are believed to be as listed, most recent first, as follows: 1. U.S. Pat. No. 6,162,930 Anti-mitotic agents which inhibit tubulin polymerization. 2. U.S. Pat. No. 5,569,786 Isolation, structural elucidation and synthesis of novel antineoplastic substances denominated "combretastatin". 3. U.S. Pat. No. 5,561,122 Combretastatin A-4 prodrug. 4. U.S. Pat. No. 5,529,989 Pancratistatin prodrug. 5. U.S. Pat. No. 5,409,953 Isolation, structural elucidation and synthesis of novel antineoplastic substances denominated "combretastatin". 6. U.S. Pat. No. 4,996,237 Combretastatin A-4. 7. U.S. Pat. No. 4,940,726 Cell growth inhibitory macrocyclic lactones denominated Combretastatin D-1 and Combretastatin D-2.

Eighteen years ago applicant reported (Pettit et al., 1982) isolation from the South African tree *Combretum caffrum* (Eckl. Zeyk.) Kuntze the first member of a series of cancer cell growth inhibitory constituents designated the combretastatins. Subsequently, applicant lead the discovery (Pettit and Singh, 1987) of combretastatin A-2 (1a) and more recently applicant has focused on improving the original synthesis of this potent inhibitor of microtubule assembly and mitosis (Lin et al., 1988 and 1989) as well as converting it to a useful phosphate prodrug (2). Those objectives form the basis of this contribution and are considered very important owing to the powerful vascular targeting (Grosior et al., 1999; Tozer et al., 1999) and anticancer properties of the closely related combretastatin A-4 (1b, Pettit et al, 1989) and its sodium phosphate prodrug (Pettit and Rhodes, 1998). The latter has led to promising results in current Phase I human cancer clinical trials (Remick et al., 1999; Rustin et al., 1999).

BRIEF DESCRIPTION OF THE INVENTION

The original synthesis of combretastatin A-2 (1a) was modified to provide an efficient scale-up procedure for obtaining this antineoplastic stilbene. Subsequent conversion to a useful prodrug was accomplished by phosphorylation employing in situ formation of dibenzylchlorophosphite 10 followed by cleavage of the benzyl ester protective groups with bromotrimethylsilane to afford phosphoric acid intermediate 11. The latter was immediately treated with sodium methoxide to complete a practical route to the disodium phosphate prodrug (2a). The phosphoric acid precursor (11) of phosphate 2a was employed in a parallel series of reactions to produce a selection of metal and ammonium cation prodrug candidates. Each of the phosphate salts (2a–q) was evaluated with respect to relative solubility behavior, cancer cell growth inhibition, and antimicrobial activity.

Accordingly a primary object of the present invention is to provide a combretastatin A-2 prodrug.

Another object of the present invention is to provide an improved method of synthesizing combretastatin A-2.

A further object of the present invention is to provide an improved method of synthesizing combretastatin A-2 prodrugs.

These and still further objects as shall hereinafter appear are readily fulfilled by the present invention in a remarkably unexpected manner as will be readily discerned from the following detailed description of an exemplary embodiment thereof especially when read in conjunction with the accompanying formulae, tables, and schemes in which like parts, and compounds, bear like numerals throughout.

DETAILED DESRCIPTION OF THE PREFERRED EMBODIMENT

In order to obtain both combretastatin A-2 (1a) and its sodium phosphate prodrug (2a) the original synthesis (Pettit and Singh, 1987) of stilbene 1a was modified. Three major improvements were employed for this purpose. Firstly, the phosphonium bromide salt and the benzaldehyde precursors used in the Wittig reaction were reversed from the original synthesis to synthetic intermediates 7 and 8, which eliminated problems associated with the formation of the triphenylphosphonium bromide derived from isovanillin. Secondly, the Wittig reaction base used to treat phosphonium bromide 7 was changed from n-butyllithium to potassium hexamethylsilylamide (KHMDS). Current evidence suggested that the presence of lithium salts favors production of the trans isomer (Reitz, 1996). Pettit and Singh, (1987), reported a Z/E ratio of 1:16 in the original Wittig sequence leading to cis-stilbene 1a. Upon substituting KHMDS and otherwise similar reaction conditions, a Z/E ratio of 1:2 was obtained. Thirdly, separation of the stilbene silyl ether protected isomers (9a and 9b) proved difficult. However, separation was readily achieved following cleavage of the silyl ether protecting group with tetrabutylammonium fluoride.

Once a practical scale-up synthesis of combretastatin A-2 (1a) and combretastatin A-2 dibenzyl phosphate ester (10) was achieved, various metal cation and ammonium salts (2a–q) of the derived phosphoric acid intermediate (11) were investigated. The various phosphate salts were synthesized to investigate the effects of different cations on both the anticancer activity of the prodrug (Table 1) and its solubility characteristics (Table II). The quinine and related ammonium cations were of interest with respect to the possibility of obtaining a stable, water-soluble drug with the ability to reverse multidrug resistance through interference with the p-glycoprotein mechanism (Chen et al., 1993; Williams & Jacobs, 1993; Kang & Perry, 1994; Adams & Knich, 1995; Genne et al., 1995; Sata et al., 1995; Watanaabe et al., 1997). The alkali metal salts (2a–d) prepared are of a dibasic nature, owing to their formation in slightly basic media (pH~9). The alkaline earth metal salts (2e–h) are of course monobasic, as are the ammonium salts (2i–q).

Combretastatin A-2 (1a) is very sparingly soluble in water (<1 mg/ml). However, as the metal phosphate salts 2a–q, the water solubility in general increased dramatically. The monovalent metal cation prodrug salts, sodium (2a, 18 mg/ml), lithium (2b, 21 mg/ml), potassium (2c,>50 mg/ml), and rubidium (2d, 40 mg/ml), all displayed good solubility in water while the divalent metal cation salts derived from zinc, calcium, magnesium, and manganese were progressively more insoluble owing perhaps to the formation of oligomers. Of the ammonium cation salts both the morpholine (2m, 41 mg/ml) and ammonium (2p, 34 mg/ml) derivatives showed good water solubility. The remaining ammonium cation salts showed low water solubility (0–1 mg/ml).

The cancer cell growth inhibitory activities (Table I) of the cation prodrugs 2a–q remained strong and corresponded closely to that of combretastatin A-2 (1a) (Table I). As expected, the colchicine salt 2n exhibited enhanced potency contributed by the cation.

Contemporaneous testing of 1a and 2a in the NCI 60-cell screen (Boyd, 1997) yielded mean-panel $GI_{50}$ values ($10^{-8}$±SE) of 8.33±1.73 and 16.5±3.07, respectively. Compare correlation analyses (Boyd & Paull, 1995) confirmed that the mean-graph profiles of combretastatin A-2 (1) and its disodium 3'-0-phosphate prodrug (2a) were essentially indistinguishable.

The combretastatins are moderately antimicrobial (Pettit et al., 1998; Pettit et al., 1995; Pettit et al., 2000; Pettit & Lippert; 2000). Combretastatin A-2 (1a) is no exception (Table III). Of the compounds screened in the present report, the parent compound (1a) and the hydroquinine salt (21) exhibited the broadest antimicrobial spectra (Table III).

Compounds were screened against the bacteria *Stenotrophomonas maltophilia, Micrococcus luteus, Staphylococcus aureus, Escherichia coli, Enterobacter cloacae, Enterococcus faecalis, Streptococcus pneumoniae, Neisseria gonorrhoeae*, and the fungi *Candida albicans* and *Cryptococcus neoformans*, according to established broth microdilution susceptibility assays (NCCLS approved standard M7-A4, 1997; NCCLS approved standard M27-A, 1997). The minimum inhibitory concentration was defined as the lowest concentration of compound that inhibited all visible growth of the test organism (optically clear). Assays were repeated on separate days.

TABLE I

Human cancer cell line activity [$GI_{50}$ (µg/ml)] and murine P388 leukemia inhibitory activity ($ED_{50}$ (µg/ml)] of combretastatin A-2 (1a), combretastatin A-2 disodium prodrug (2a) and other prodrug salts (2b–q).

| Structure | Pancreas BXPC-3 | Breast MCF-7 | CNSGliob SF5268 | Lung-NSC NCI-H460 | Colon KM20L2 | Prostrate DU-145 | Leukemia P388 |
|---|---|---|---|---|---|---|---|
| 1a | 0.014 | 0.0042 | 0.0083 | 0.043 | 0.47 | 0.0054 | 0.016 |
| 2a | 2.1 | 0.045 | 0.042 | 0.41 | 3.8 | 0.053 | 0.0250 |
| 2b | 4.7 | 0.33 | 0.15 | 0.36 | 2.4 | 0.32 | 0.0432 |
| 2c | 3.0 | 0.47 | 0.38 | 0.44 | 2.5 | 0.47 | 0.0728 |
| 2d | 5.2 | 0.43 | 0.35 | 0.44 | 3.1 | 0.40 | 0.132 |
| 2e | 6.6 | 0.045 | 0.015 | 0.38 | 8.8 | 0.071 | 0.0602 |
| 2f | 11.8 | 2.6 | 0.22 | 2.8 | 16.6 | 1.1 | 0.194 |
| 2g | 8.3 | 1.1 | 0.23 | 2.7 | 8.8 | 0.37 | 0.146 |
| 2h | 3.9 | 0.66 | 2.3 | 2.5 | 2.1 | 3.0 | 0.0379 |
| 2i | 2.4 | 0.35 | 0.40 | 0.51 | 2.1 | 0.38 | 0.220 |
| 2j | 3.1 | 0.27 | 0.11 | 0.34 | 2.0 | 0.27 | 0.0322 |
| 2k | 0.0098 | 0.0047 | 0.017 | 0.021 | 0.011 | 0.021 | <0.0100 |
| 2l | 3.9 | 0.065 | 0.029 | 1.4 | 3.4 | 0.029 | 0.0405 |
| 2m | 2.8 | 0.057 | 0.030 | 0.18 | 3.6 | 0.044 | 0.0149 |
| 2n | 5.1 | 0.44 | 0.59 | 0.42 | 3.0 | 0.45 | 0.203 |
| 2o | 2.7 | 0.44 | 0.52 | 0.89 | 2.5 | 0.41 | 0.263 |
| 2p | 3.0 | 0.068 | 0.063 | 0.36 | 3.0 | 0.075 | 0.0307 |
| 2q | 3.3 | 0.38 | 0.48 | 0.64 | 2.8 | 0.45 | 0.272 |

TABLE II

Solubility of combretastatin A-2 (1a), combretastatin A-2 disodium phosphate prodrug (2a) and other prodrug salts (2b–q) in water (mg/ml) at 25° C.

| | 1a | 2a | 2b | 2c | 2d | 2e | 2f | 2g | 2h | 2i | 2j | 2k | 2l | 2m | 2n | 2o | 2p | 2q |
|---|---|---|---|---|---|---|---|---|---|---|---|---|---|---|---|---|---|---|
| mg/ml | <1 | 18 | 21 | >50 | 40 | <1 | <1 | 3 | <1 | <1 | 5 | <1 | <1 | 41 | 1 | 2 | 34 | <1 |

TABLE III

Antimicrobial activities of combretastatin A-2 and prodrugs in the broth microdilution assay

| Compound | Microbe(s) inhibited | Minimum inhibitory concentration (μg/ml) |
|---|---|---|
| 1a | *Cryptococcus neoformans* | 64 |
|  | *Streptococcus pneumoniae* | 64 |
|  | *Micrococcus luteus* | 64 |
|  | *Neisseria gonorrhoeae* | 32 |
| 2a | *N. gonorrhoeae* | 8 |
| 2b | *N. gonorrhoeae* | 16 |
| 2c | *N. gonorrhoeae* | 16 |
| 2d | *N. gonorrhoeae* | 16 |
| 2e | *N. gonorrhoeae* | 4 |
| 2f | *N. gonorrhoeae* | 16 |
| 2g | *N. gonorrhoeae* | 8 |
| 2h | *N. gonorrhoeae* | 4 |
| 2i | *S. pneumoniae* | 16 |
|  | *N. gonorrhoeae* | 32 |
| 2j | *N. gonorrhoeae* | 16 |
| 2k | *M. luteus* | 64 |
|  | *N. gonorrhoeae* | 16 |
| 2l | *C. neoformans* | 16 |
|  | *S. pneumoniae* | 8 |
|  | *M. luteus* | 32 |
|  | *N. gonorrhoeae* | 8 |
| 2m | *N. gonorrhoeae* | 16 |
| 2n | *N. gonorrhoeae* | 64 |
| 2o | *N. gonorrhoeae* | 8 |
| 2p | *N. gonorrhoeae* | 16 |
| 2q | *N. gonorrhoeae* | 4 |

Scheme 1ª

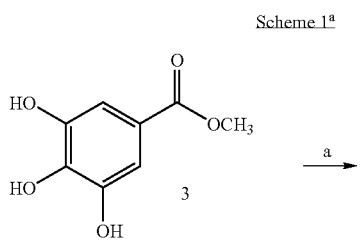

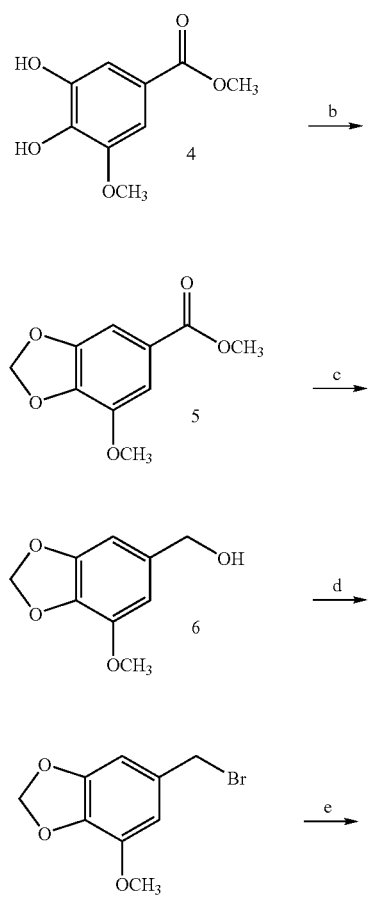

ªReagents and Conditions: a) Borax, NaOH, DMS, H$_2$O, rt, 12 h; b) CsF, CH$_2$Br$_2$, DMF, 110° C., 12 h, Ar; c) LiAlH$_4$, THF, rt, 3 h, Ar; d) PBr$_3$, DCM, 0° C., 6 h, Ar; d) PPh$_3$, Toluene, 110° C., 12 h, Ar Scheme 2ª

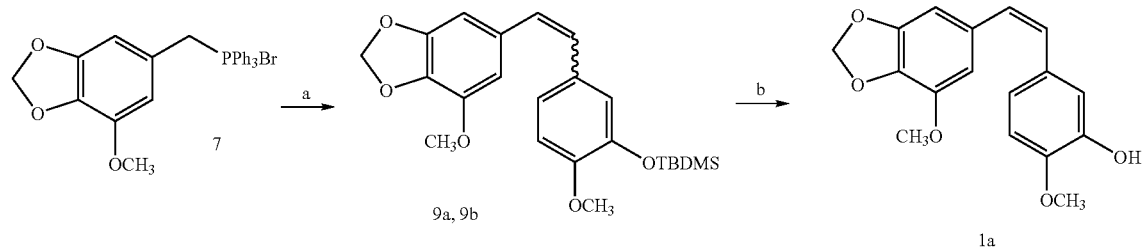

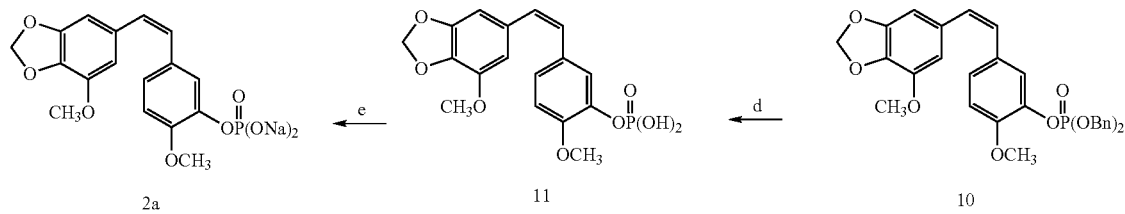

2a             11             10

[a]Reagents and Conditions: a) KHMDS, 3-O-TBDMS-4-methoxybenzaldehyde, THF, -78° C., 12 h, Ar; b) TBAF, THF, 0° C., 6 h, Ar; c) CCl$_4$, DMAP, DIEA, P(H)(O)(OBn$_2$), CH$_3$CN, -10° C., 6 h, Ar; d) TMS-Br, DCM, 30 min, Ar; e) NaOCH$_3$, CH$_3$CH$_2$OH, 0° C., Ar Ether refers to diethyl ether and Ar to argon gas. All solvents were redistilled. Dimethylformamide (DMF), lithium aluminum hydride, tetrahydrofuran (THF), triphenylphosphine, diisopropylethylamine (DIEA), potassium hexamethylsilylamide (KHMDS), carbon tetrachloride, tetrabutylammonium fluoride (TBAF), dibenzylphosphite, 4-dimethylaminopyridine (DMAP), bromotrimethylsilane and acetonitrile were obtained from the Sigma-Aldrich Chemical Company (Milwaukee, Wis.). Magnesium acetate tetrahydrate, calcium acetate, manganese acetate, quinidine, quinine, hydroquinine, and concentrated hydrochloric acid were supplied by the Baker Chemical Company. Nicotinamide was purchased from the Alexis Corporation and all other reagents from Acros Organics (Fisher Scientific, Pittsburgh, Pa.).

Reactions were monitored by thin-layer chromatography using Analtech silica gel GHLF Uniplates visualized under long-wave (366 nm) and short-wave (254 nm) UV irradiation. Solvent extracts of aqueous solutions were dried over anhydrous sodium sulfate. Where appropriate, the crude products were purified by silica gel column chromatography, flash (230–400 Mesh ASTM) or gravity (70–230 Mesh ASTM) silica gel from E. Merck.

Melting points were measured with an electrothermal digital melting point apparatus (Model IA9200) and are uncorrected. The IR spectra were obtained using a Mattson Instruments 2020 Galaxy Series FT-IR. EIMS data were recorded with a MAT 312 mass spectrometer, and high-resolution FAB spectra were obtained with a Kratos MS-50 mass spectrometer All $^1$H-NMR spectra were recorded using a Varian Gemini 300 MHz instrument with CDCl$_3$ (TMS internal reference) as solvent unless otherwise noted. The $^{13}$C- and $^{31}$P-NMR spectra were obtained using a Unity 500 MHz instrument with CDCl$_3$ as solvent unless otherwise noted. Bs refers to broad singlet and bd refers to broad doublet.

A practical synthetic procedure for the production of both combretastatin A-2 (1a) and prodrugs (e.g. 2a) was devised based on our original synthesis of stilbene 1a (Pettit and Singh, 1987). Synthesis of the sodium phosphate (2a) and other prodrugs (2b–q) resulted from treating phenol 1a with dibenzyl phosphite (Silverberg et al., 1996) to yield the corresponding bis(benzyl) phosphate. Cleavage of the benzyl protecting groups with bromotrimethylsilane (Lazar and Guillaumet, 1992) and subsequent treatment of the phosphoric acid with the appropriate cation precursor (sodium methoxide in the case of 2a) readily afforded prodrugs 2a–q.

The phosphate derivatives were chosen for three reasons. Firstly, the phosphate salts enjoy enhanced solubility characteristics (Bundgaard, 1991). Secondly, once administered, phosphate prodrugs are believed to be primarily dephosphorylated in the tumor to yield the parent compound via non-specific phosphatases and are then transported intracellularly (Pettit et al., 1995a; Pettit and Rhodes, 1998). Thirdly, as the phosphate salt, the parent compound should be less susceptible to isomerization to the less active E-stilbene. The E-isomer of combretastatin A-2 shows considerably less antimitotic activity (Lin et al., 1988) than the Z-isomer (1a). Prodrugs based on a phosphate group have proven useful for improving other anticancer drugs, such as pancratistatin, taxol, tyrosine-containing peptides, and etoposide (Pettit et al., 1995b; Ueda et al., 1993; Vyas et al., 1993; Chao et al., 1993; Saulinier et al., 1994).

The following procedures for obtaining intermediates 4–6 represent relatively minor but useful modifications of our original methods (Pettit and Singh, 1987).

Methyl 3,4-dihydroxy-5-methoxybenzoate (4)

To a stirred mixture of sodium borate decahydrate (borax, 80 g) in H$_2$O (1 L) was added methyl gallate (3, 15.0 g, 82 mmol) at rt. After stirring for 1 h, dimethyl sulfate (30 ml, 317 mmol) and NaOH (50 ml, 6.5 M) were added dropwise simultaneously via separate addition funnels over the course of 1 h. After stirring an additional 12 h, the methylation was terminated with H$_2$SO$_4$, (65 ml, conc.) and stirring continued an additional h. The product was removed by extraction with DCM (5×500 ml, each time stirring the solution for 20 min). The combined DCM extracts were washed with brine (300 ml), dried, concentrated in vacuo, and the residue crystallized from methanol-benzene to afford methyl ether 4 (13.7 g, 85%) as a light tan solid, mp 110–111° C., (lit. mp 110–111° C., Pettit and Singh, 1987); $^1$H-NMR (300 MHz): 3.89 (3H, s, —OCH$_3$), 3.94 (3H, s, —OCH$_3$), 5.40 (2H, bs, —OH), 5.80 (2H, bs, —OH), 7.22 (1H, d, J=1.8 Hz, ArH), 7.35 (1H, d, J=1.8 Hz, ArH).

Methyl 3,4-methylenedioxy-5-methoxybenzoate (5)

Cesium fluoride (26.5 g, 174 mmol) was added quickly to a stirred solution of diol 4 (7.7 g, 39 mmol) in DMF (80 ml) at rt under Ar. After stirring for 1 h, dibromomethane (5.4 ml, 78 mmol) was added dropwise at rt and the mixture heated to 110° C. for 12 h. Upon cooling to rt, ether (300 ml) was added and the mixture washed with cold water (3×50 ml). The combined aqueous phase was then extracted with ether (2×100 ml), dried and concentrated in vacuo. The resultant crude residue was absorbed onto silica gel (gravity) and purified via silica gel chromatography (gravity, 1:5; EtOAc in n-hexane), affording methylenedioxy derivative 5 (8.1 g, 99%) as a colorless powder; m.p. 89–91° C. (mp 89–91° C., Pettit and Singh, 1987); $^1$H-NMR (300 MHz):

3.89 (3H, s, —OCH₃), 3.94 (3H, s, —OCH₃), 6.05 (2H, s, —OCH₂O—), 7.21 (1H, d,J=1.8 Hz, ArH), 7.33 (1 H, d, J=1.8 Hz, ArH).

3,4-Methylenedioxy-5-methoxybenzyl alcohol (6)

Methyl ester 5 (11.9 g, 57 mmol) in THF (50 ml) was added (slowly) dropwise to a stirred grey suspension of lithium aluminum hydride (3.4 g, 90 mmol) in THF (50 ml) at 0° C. under Ar. After stirring for 3 h at rt, the suspension was cooled to 0° C. and the reduction terminated by careful addition of Na₂SO₄ (sat., aq) until effervescence ceased. The precipitate was collected and the filtrant dried and concentrated in vacuo to afford benzyl alcohol 6 (9.3 g, 91%) as a colorless powder, m.p. 66–67° C. (lit. mp 66–67° C., Pettit and Singh, 1987); ¹H-NMR (300 MHz):1.59 (1H, bs, —OH), 3.91 (3H, s, —OCH₃) 4.59 (2H, bs, —ArCH₂O—), 5.97 (2H, s, —OCH₂O—), 6.56 (2H, d, J=2.1 Hz, ArH).

3,4-Methylenedioxy-5-methoxybenzyltriphenylphosphonium bromide (7)

To a stirred solution of benzyl alcohol 6 (31.9 g, 175 mmol) in DCM (250 ml) was added (at 0° C. under Ar) dropwise phosphorous tribromide (20.0 ml, 213 mmol). After stirring for 8 h, the bromination was terminated with NaHCO₃ (10%, aq, at 0° C.). The organic phase was dried and concentrated in vacuo, affording the benzyl bromide intermediate as a light brown solid. The benzyl bromide was immediately dissolved in toluene (350 ml) and triphenylphosphine (45.8 g, 175 mmol) added under Ar at rt. Upon stirring for 30 min, the mixture was heated to reflux for 12 h. After cooling to rt, the white suspension was filtered and the solid triturated with ether, which was then recrystallized from ethanol to afford phosphonium salt 7 (82.2 g, 93%) as colorless crystals, m.p. 241–243° C., ¹H-NMR (300 MHz, CD₃OD):3.54 (3H, s, —OCH₃) 4.84 (2H, s, ArCH₂P—), 5.91 (2H, s, —OCH₂O—), 6.14 (1H, bs, ArH), 6.18 (1H, bs, ArH), 7.70 (15H, m, Ph₃); ¹³C-NMR (500 MHz, DMSO-d₆): 28.14, 28.52, 55.99, 101.59, 104.54, 110.71, 117.41, 118.09, 121.20, 121.27, 130.03, 130.12, 134.05, 134.12, 134.80, 135.06, 142.90, 148.49, ³¹P-NMR (500 MHz, DMSO-d₆): 25.75; IR (KBr): 3639, 3005, 2845, 1631, 1510, 1448, 1313, 1091, 1035; HRMS m/z 427.1461 [M-Br]⁺; Anal calcd for C₂₇H₂₄O₃PBr: C, 63.92; H, 4.77. Found: C, 62.60; H, 5.30.

3'-O-TBDMS-E,Z-Combretastatin A-2 (9a, 9b)

To a stirred suspension of phosphonium bromide 7 (40.0 g, 78.8 mmol) in THF (250 ml at rt under Ar) was added 18-crown-6 (55.5 g, 210 mmol). Upon stirring for 30 min, the suspension was cooled to −10° C. and KHMDS (160.0 ml, 160.0 mmol, 0.5 M soln, in THF) added dropwise over the course of 45 min. Upon stirring an additional 3 h at rt, the dark red mixture was cooled to −78° C. and 3-0-TBDMS-4-methoxybenzaldehyde 8 (20.0 g, 75.0 mmol, Pettit and Rhodes, 1998) added dropwise as a solution in THF (75 ml) over the course of 1 h. After stirring for 12 h at rt the Wittig reaction was stopped by addition of H₂O (200 ml) and stirred for another 45 min. The phases were separated and the aqueous phase extracted with ethyl acetate (5×300 ml). The combined organic extract was dried and concentrated in vacuo. The resultant oil was absorbed onto silica gel (gravity) and subjected to separation by silica gel chromatography (flash, 1:9; EtOAc in n-hexane). The Z (9a) and E (9b) olefins were collected as a mixture (31.3 g, 96%). ¹H-NMR analysis of the mixture indicated a Z:E ratio of 2:5.

Combretastatin A-2 (1a)

Tetrabutylammonium fluoride (55.0 ml, 55.0 mmol) was added (at 0° C. under Ar) to a stirred solution of the Z and E (9a, 9b) isomers (19.1 g, 46.1 mmol) in THF (100 ml). After stirring for 6 h, the desilylation was complete and HCl (75 ml, 6M at 0° C.) slowly added. Upon stirring for 30 min, the solution was extracted with ethyl acetate (5×200 ml). The combined organic extract was dried and concentrated in vacuo. The resultant oil was absorbed onto silica gel (gravity) and separated by silica gel chromatography (flash, 1:9; EtOAc in n-hexane). The Z phenol (1a) was collected as a clear oil (4.69 g, 34%); ¹H-NMR (300 MHz): 3.75 (3H, s, —OCH₃), 3.87 (3H, s, —OCH₃), 5.93 (2H, s, —OCH₂O—), 6.39 (1H, d, J=12.0 Hz), 6.41 (1H, d, J=12.0 Hz), 6.46 (1 H, bs, H-2), 6.49 (1H,bs, H-6), 6.75 (1 H, d, J=8.4 Hz, H-5'), 6.76 (1H, bd, J=8.4 Hz, H-6'), 6.87 (1H, bs, H-2'). In addition, a mixture of Z and E phenols (3.17 g, 23%) and the pure E phenol (5.06 g, 37%) was obtained.

3'-O-Bis(benzyl)phosphoryl-Z-combretastatin A-2 (10)

To a stirred solution of combretastatin A-2 (1a, 9.29 g, 30.9 mmol) in acetonitrile (70 ml) under Ar at −10° C. was added (dropwise) carbon tetrachloride (15.0 ml, 155 mmol). Following stirring for 10 min, diisopropylethylamine (11.0 ml, 63.0 mmol) and 4-dimethylaminopyridine (cat) were added. Five minutes later, dibenzyl phosphite (11.6 ml, 52.5 mmol) was added (slowly dropwise at −10° C.). Upon stirring for 5 h, the phosphorylation was terminated by dropwise addition of KH₂PO₄ (50 ml, 0.5 M). The mixture was extracted with ethyl acetate (4×50 ml). The combined organic extract was dried, concentrated in vacuo, and the oily residue absorbed onto silica (gravity) and separated by silica gel chromatography (flash, 1:4; EtOAc in n-hexane) to afford phosphate 10 as a light tan oil (15.5 g, 90%); ¹H-NMR (500 MHz): 3.72 (3H, s, —OCH₃), 3.77 (3H, s, —OCH₃), 5.12 (2H, s, —OCH₂Ar), 5.14 (2H, s, —OCH₂Ar), 5.85 (2H, s, —OCH₂O—), 6.35 (1H, d, J=12.0 Hz), 6.41 (1H, d, J=12.0 Hz), 6.44 (1H, bs, H-2), 6.45 (1H, bs, H-6), 6.79 (1H, d, J=6.3 Hz, H-5'), 7.05 (1H, bd, J=6.3 Hz, H-6'), 7.14 (1H, bs, H-2'), 7.31 (10H, s, ArH); ¹³C-NMR (500 MHz): 55.90, 56.31, 69.68, 101.26, 102.83, 108.22, 112.25, 121.99, 126.39, 127.74, 128.13, 128.35, 129.28, 129.94, 131.38, 134.27, 135.60, 135.67, 139.31, 139.39, 143.30, 148.53, 149.63; ³¹P-NMR (500 MHz): −7.81; IR (KBr): 3055, 2985, 2685, 2307, 1622, 1512, 1427, 1267, 1130, 998; HRMS m/z 560.16 [M]⁺; Anal calcd for C₃₁H₂₉O₈P: C, 66.42; H, 5.21. Found: C, 66.31; H, 5.24.

Sodium combretastatin A-2 3'-O-phosphate (2a)

Procedure A. To a stirred solution of dibenzyl ester 10 (0.38 g, 0.678 mmol) in DCM (5 ml) under Ar at 0° C. was added bromotrimethylsilane (0.185 ml, 1.40 ml). After stirring for 45 min, sodium thiosulfate (1% aq. soltn., 5 ml) was added and the mixture stirred an additional 5 min. The phases were separated and the aqueous phase extracted with ethyl acetate (3×5 ml). The combined organic extract was concentrated in vacuo to afford the phosphoric acid intermediate as a clear oil. After drying (high vacuum) for 1 h, the oil was immediately dissolved in ethanol (10 ml) and sodium methoxide (74 mg, 1.37 mmol) added (at 0° C.) at once. After stirring for 30 min, the precipitate was collected and triturated with ether to afford sodium salt 2a as a colorless powder. Recrystallization from water-acetone yielded 2a (0.24 g, 84%) as colorless crystals; m.p. 125–126° C.; ¹H-NMR (500 MHz, DMSO-d₆): 3.67 (3H, s, —OCH₃), 3.69 (3H, s, —OCH₃), 5.93 (2H, s, —OCH₂O—), 6.32 (1H, d, J=12.0 Hz), 6.38 (1H, d, J=12.0 Hz), 6.44 (1H, bs, H-2), 6.56 (1H, bs, H-6), 6.75 (2H, m, H-5', H-6'), 7.44 (1H, bs, H-2'), ¹³C-NMR (500 MHz, DMSO-d₆): 55.56, 55.99, 101.08, 102.17, 108.50, 111.98, 120.77. 121.11, 127.92, 128.86, 129.38, 131.41, 133.84, 142.92, 143.91, 148.10, 149.20, 149.25; $^{31}$P-NMR (500 MHz, DMSO-$d_6$):–1.59: IR (KBr): 3528, 2972, 2880, 1632, 1512, 1449, 1323, 1267, 1180, 1117, 1038, 932; and HRMS m/z 425.04 $[M+H]^+$.

Procedure B. A solution of dibenzyl ester 10 (9.0 g, 16.1 mmol) in DCM (40 ml) was stirred at rt and bromotrimethylsilane (4.50 ml, 34.1 mmol) was added (dropwise). After 35 min, water (20 ml) was added and stirring continued an additional 5 min. The aqueous phase was extracted with ethyl acetate (3×20 ml). The combined organic extract was concentrated in vacuo to yield the phosphoric acid as a clear oil, which was immediately dissolved in ethanol (40 ml). Sodium methoxide (1.75 g, 32.4 mmol) was added (at 0° C.) at once. Thirty-five min later, the precipitate was collected and triturated with ether to provide sodium phosphate 2a as a colorless powder. Recrystallization from water-acetone yielded phosphate prodrug 2a (5.8 g, 85%) as colorless crystals. However, procedure B generally led to separation problems owing to partial conversion of cis to the trans geometry during the reaction/isolation steps. The trans isomer was found to melt at 161–162° C. following recrystallization from water-acetate and exhibited a trans $^1$H-NMR (300 MHz) coupling constant of 16.4 Hz.

In order to obtain both combretastatin A-2 (1a) and its sodium phosphate prodrug (2a) in quantity, a modified synthesis process (Pettit and Singh, 1987) of stilbene 1a was employed. As stated above, at least three major improvements were employed for this purpose. Firstly, the phosphonium bromide salt and the benzaldehyde precursors used in the Wittig reaction were reversed from the original synthesis to synthetic intermediates 7 and 8, respectively. That eliminated problems associated with the formation of the triphenylphosphonium bromide derived from isovanillin.

Secondly, the Wittig reaction base used to treat phosphonium bromide 7 was changed from n-butyllithium to potassium hexamethylsilylamide (KHMDS). Current evidence suggested that the presence of lithium salts favors production of the trans isomer (Reitz, 1996). Pettit and Singh, (1987), reported a Z/E ratio of 1:16 in the original Wittig sequence leading to cis-stilbene 1a. Upon substituting KHMDS and otherwise similar reaction conditions, a Z/E ratio of 1:2 was obtained. Thirdly, separation of the stilbene silyl ether protected isomers (9a and 9b) proved difficult.

Despite the difficulties described above, usable water soluble prodrugs of combretastatin A2 were obtained. If obtained in usable quantities, applicant believes that the compounds could be used in the manner described below, as antineoplastic compounds.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, that the presence of lithium salts favors production of the trans isomer (Reitz, 1996). Pettit and Singh, (1987), reported a Z/E ratio of 1:16 in the original Wittig sequence leading to cis-stilbene 1a. Upon substituting KHMDS and otherwise similar reaction conditions, a Z/E ratio of 1:2 was obtained. Thirdly, separation of the stilbene silyl ether protected isomers (9a and 9b) proved difficult.

Despite the difficulties described above, usable water soluble prodrugs of combretastatin A2 and combretastatin A4 were obtained. If obtained in usable quantities, applicant believes that the compounds could be used in the manner described below, as antineoplastic compounds.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies a prodrug of combretastatin A2, combretastatin A4, or any other compound described herein.

Composition "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| | |
|---|---|
| Active ingredient, micronized | 200 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | |
|---|---|
| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| | |
|---|---|
| Active ingredient, micronized | 15 g |
| POLYSORBATE 80 | 5 g |
| Methylparaben | 2.5 g |
| Propylparaben | 0.17 g |
| Deionized water, q.s. | 1000 ml |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition "J"

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

We claim:

1. A method for synthesizing combretastatin A-2 or A-4 prodrugs, comprising the steps of:
   (a) treating combretastatin A-2 with dibenzyl phosphite to yield a bis(benzyl) phosphate;
   (b) treating the bis(benzyl) phosphate to cleave the benzyl protecting groups, to form a phosphoric acid intermediate; and
   (c) treating the resulting phosphoric acid intermediate with an appropriate cation precursor, to form said prodrugs.

2. The method of claim 1 wherein the benzyl protecting groups are cleaved using bromotrimethylsilane.

3. The method of claim 1 wherein in step (b) the phosphoric acid precursor is treated with sodium methoxide.

* * * * *